United States Patent [19]
Abichandani et al.

[11] Patent Number: 5,977,420
[45] Date of Patent: Nov. 2, 1999

[54] DUAL-LOOP XYLENE ISOMERIZATION PROCESS

[75] Inventors: Jeevan S. Abichandani, Voorhees; Jeffrey S. Beck, Burlington; Stephen H. Brown, Princeton; Ronald J. Cimini, Sewell; Ivy D. Johnson, Lawrenceville; Dimitris K. Liguras, Mantua; David L. Stern, Mount Laurel, all of N.J.

[73] Assignee: Mobil Oil Corporation, Fairfax, Va.

[21] Appl. No.: 09/139,463

[22] Filed: Aug. 25, 1998

[51] Int. Cl.⁶ .............................. C07C 1/00; C07C 5/22
[52] U.S. Cl. .................... 585/319; 585/313; 585/478; 585/477; 585/481; 585/479
[58] Field of Search ................... 585/478, 479, 585/477, 481, 313, 314, 315, 319

[56] References Cited

U.S. PATENT DOCUMENTS

| | | | |
|---|---|---|---|
| 3,948,758 | 4/1976 | Bonacci et al. | 208/92 |
| 4,016,219 | 4/1977 | Kaeding | 260/672 T |
| 4,160,788 | 7/1979 | Young | 585/475 |
| 4,182,923 | 1/1980 | Chu | 585/475 |
| 4,723,049 | 2/1988 | Menard et al. | 585/475 |
| 4,899,011 | 2/1990 | Chu et al. | 585/481 |
| 4,922,055 | 5/1990 | Chu | 585/470 |
| 4,956,511 | 9/1990 | Butler et al. | 585/475 |
| 5,387,732 | 2/1995 | Shamshoum et al. | 585/475 |
| 5,475,180 | 12/1995 | Shamshoum et al. | 585/475 |
| 5,516,956 | 5/1996 | Abichandani et al. | 585/481 |
| 5,625,104 | 4/1997 | Beck et al. | 585/475 |
| 5,689,027 | 11/1997 | Abichandani et al. | 585/481 |
| 5,705,726 | 1/1998 | Abichandani et al. | 585/481 |

*Primary Examiner*—Walter D. Griffin
*Assistant Examiner*—Thuan D. Dang
*Attorney, Agent, or Firm*—Peter W. Roberts; Malcolm D. Keen

[57] ABSTRACT

A method for increasing the efficiency of xylene isomerization by using a two stage isomerization process. In the first stage of the process, a $C_9^+$ aromatics feedstock is subjected to ethylbenzene conversion and xylene isomerization. Non-$C_8$ aromatics are removed from the effluent, which is then processed in a second stage of the process to remove para-xylene and isomerize the para-xylene depleted effluent. The effluent from the second stage isomerization unit is then recycled into the inlet of the second stage of the process and a slip stream from the para-xylene separator is recycled to the feedstock and to the effluent of the ethylbenzene conversion unit. In this way, the production of para-xylene is maximized. In a preferred embodiment, toluene is co-fed into the feedstock to minimize the loss of xylenes during the ethylbenzene conversion reaction.

10 Claims, 3 Drawing Sheets

DUAL-LOOP XYLENE ISOMERIZATION PROCESS

BACKGROUND OF THE INVENTION

This invention is a method for increasing the efficiency of xylene isomerization in a process for the catalytic conversion of ethylbenzene coupled with xylene isomerization. More specifically, the invention increases the efficiency of xylene isomerization by using a two stage isomerization process.

Xylenes and ethylbenzene are $C_8$ benzene homologues having the molecular formula $C_8H_{10}$. The three xylene isomers are ortho-xylene, meta-xylene and para-xylene, which differ in the positions of two methyl groups on the benzene ring. The term mixed xylenes describes a mixture of ethylbenzene and the three xylene isomers. Mixed xylenes are largely derived from petroleum.

Para- and ortho-xylenes are valuable chemical intermediates. In the petrochemical complex, they are produced in large part by recovery of these compounds from both the crude distillation and the $C_8$ heart cut of the reformer. Recovery is accomplished via several selective separation processes, such as $C_8$ heart-cut distillation to yield high-purity ortho-xylene "ortho-splitter"), and selective crystallization or sorption processes. The remainder from these separation technologies involves mostly meta- and ortho-xylenes, ethylbenzene, and benzene, with relatively low concentrations of other aromatics.

Several technologies exist for upgrading the chemical value of this recycle stream. For example, there are commercial processes for converting this stream into one containing an equilibrium mixture of xylenes—that is, roughly 50 weight percent (wt %) meta-xylene, and 25 wt % each of para- and ortho-xylenes—via isomerization. These processes also reduce the ethylbenzene concentration in this recycle loop through mechanisms such as cracking, or hydrocracking (hydrogenation of the ethylene thus formed from ethylbenzene cracking by means of a functional metal).

Although these processes have been practiced commercially for many years, great improvements could be realized if it were possible to significantly reduce the capital costs of the isomerization complex. The commercial processes that are presently being used require large capacity processing vessels to produce a relatively small amount of product. Therefore, it is desirable to find a method that increases the amount of product that can be produced by existing equipment and also allow new plants using smaller capacity equipment to produce the equivalent amount of product.

The various xylenes may be derived from mixtures of $C_8$ aromatics separated from such raw materials as petroleum naphthas, particularly reformates, usually by selective solvent extraction. The $C_8$ aromatics in such mixtures and their properties are shown below:

| | Freezing Point (° C.) | Boiling Point (° C.) | Density (Kg/m³) | Equilibrium* Proportion (wt %) |
|---|---|---|---|---|
| Ethylbenzene | −95.0 | 136.2 | 869.9 | 8.5 |
| Para-xylene | 13.2 | 138.5 | 863.9 | 22.3 |
| Meta-xylene | −47.4 | 138.8 | 866.3 | 48.0 |
| Ortho-xylene | −25.4 | 144.0 | 883.1 | 21.2 |
| | | | Total | 100.0 |

*Calculated thermodynamic equilibria at 850° F. (454° C.).

Principal sources of $C_8$ aromatics mixtures are catalytically reformed naphthas and pyrolysis distillates. The $C_8$ aromatic fractions from these sources vary quite widely in composition but will usually be in the range of 10 wt % to 32 wt % ethylbenzene (EB) with the balance being about 50 wt % meta-xylene and about 25 wt % each of para-xylene and ortho-xylene.

Individual isomer products may be separated from the naturally occurring mixtures by appropriate physical methods. Ethylbenzene may be separated by fractional distillation, although this is a costly operation. Ortho-xylene may be separated by fractional distillation, and it is so produced commercially. Para-xylene may be separated from the mixed isomers by fractional crystallization, selective adsorption, or membrane separation.

As shown above, the boiling point of ethylbenzene is very close to those of para-xylene and meta-xylene. As a result, complete removal of ethylbenzene from the $C_8^+$ aromatics mixture by conventional methods, e.g., distillation, is usually impractical. An ethylbenzene separation column may be used in the isomerizer-separator loop or the ethylbenzene may be converted catalytically in the isomerizer-separator loop.

In many processes for xylene isomerization, the conversion of ethylbenzene is not maximized because of the need to control the competing reactions which convert xylenes to less valuable compounds. Thus, when ethylbenzene is catalytically converted, the primary consideration for selecting the operating conditions is to minimize xylene losses from transalkylation of xylenes.

The present invention enhances the efficiency of producing xylenes for ethylbenzene conversion/xylene isomerization processes that are presently being used. The present invention also provides higher production of para-xylene in an ethylbenzene conversion/xylene isomerization process by using a two stage isomerization process to more efficiently isomerize xylenes.

SUMMARY OF THE INVENTION

It has now been discovered that the problems encountered in the prior art can be overcome by the present invention, which provides a method for increasing the efficiency of xylene isomerization of a $C_8^+$ feedstock in a xylene isomerization processing scheme including: subjecting the feedstock to ethylbenzene conversion in a first stage of the scheme to provide a first effluent stream; removing $C_9^+$ aromatics and, optionally, ortho-xylene, from the first effluent stream to provide a first depleted stream; recovering para-xylene from the first depleted stream to provide a second depleted stream; isomerizing xylenes in the second depleted stream to provide a second effluent stream; and recycling the second effluent stream into the first depleted stream prior to the recovery of para-xylene.

In a preferred embodiment of the present invention benzene and toluene are removed from the first depleted stream prior to the para-xylene recovery. The toluene is then either recycled into the feedstock or taken off as a by-product of the process.

In another preferred embodiment of the present invention, a slip stream is taken from the second depleted stream after para-xylene is recovered and prior to the isomerization stage, and recycled into the feedstock. Para-xylene recovery is accomplished by selective sorption and/or crystallization. In another preferred embodiment, a slip stream is taken from the second depleted stream after para-xylene is recovered and prior to the isomerization stage, and recycled into the first effluent stream after ethylbenzene conversion. In a most preferred embodiment, two slip streams are taken from the second depleted stream after para-xylene is recovered and prior to the isomerization stage. The first slip stream is recycled into the feedstock and the second slip stream is recycled into the first effluent stream.

In a preferred embodiment the present invention, the catalysts used in the ethylbenzene conversion unit and, optionally, the xylene isomerization unit utilize one or more intermediate pore size molecular sieves. The molecular sieves can contain at least one metal selected from the group consisting of Pt, Pd, Ni, Rd, Fe, W and Re.

In a particularly preferred embodiment of the present invention, the first stage of the process further comprises xylene isomerization. The xylene isomerization can be accomplished in a dual-bed reactor, wherein the ethylbenzene conversion takes place in the first section of the reactor and the xylene isomerization takes place in the second section of the reactor, or in a separate reactor that is preferably located immediately downstream of the ethylbenzene conversion reactor. For either configuration, catalysts are selected to maximize the production of xylenes. Catalysts for the ethylbenzene conversion reactor are selected to provide the maximum conversion of ethylbenzene with the minimum loss of xylenes. Catalysts for the isomerization reactor are selected so that the xylenes in the first effluent stream are substantially isomerized to equilibrium.

In another preferred embodiment of the present invention, the toluene is added to the feedstock prior to the first stage to minimize the loss of xylene during the ethylbenzene conversion stage of the process. The toluene can be added from a source external to the process, or by co-feeding toluene recovered from the first effluent stream. In some cases, toluene can be obtained from a combination of an external source and toluene recovered from the first effluent stream. After the toluene has been added, the preferred toluene concentration in the feedstock is between about 1% and 25% by weight. A most preferred toluene concentration in the amended feedstock is at least 5 wt % of the feedstock.

In a most preferred embodiment of the present invention, the toluene is added so as to increase the ratio of toluene to xylenes in the feedstock. Preferably, the ratio of toluene to xylenes in the feedstock is increased to a range of from about 1 to 10 to about 1 to 2. The most preferred range is about 1 to 4 to about 1 to 6.

The dual stage process has the advantage of isomerizing xylenes more efficiently than a single stage process. The first ethylbenzene conversion/isomerization stage converts the ethylbenzene in the feedstock to benzene and ethane. The effluent is processed to remove $C_9^+$ aromatics, and optionally ortho-xylene, to provide a first depleted stream and then processed to remove benzene, toluene and lighter hydrocarbons to provide a second depleted stream. Thus, when the second depleted stream is processed in the second isomerization stage, the volume of the effluent from the first ethylbenzene conversion/isomerization stage is reduced and the effluent is rich in the xylenes that are targeted by the process. Accordingly, the vessels in the second isomerization stage can be smaller and operate more efficiently.

The recycle loop in the second isomerization stage, which recycles the second effluent stream into the first depleted stream, also provides the advantage of maximizing the production of para-xylene. Since ortho-xylene and meta-xylene are not removed from the process during the second isomerization stage, the xylene rich effluent stream is recycled until all of the xylenes are either converted to para-xylene, or are removed from the process as lower order hydrocarbons in the benzene/toluene separator.

The slip stream that recycles the second depleted stream provides a means for removing any $C_9^+$ aromatics and ortho-xylene from the second depleted stream and also provides a means for controlling the recycle flow of the second effluent stream. Up to 50% of the second depleted stream can be recycled through the slip stream and the most preferred range is from about 5% to about 25%. The slip stream is either recycled into the feedstock or the first effluent stream. In a most preferred embodiment of the invention, the slip stream is divided into two recycle slip streams; the first stream is recycled into the feedstock and the second stream is recycled into the first effluent stream.

Accordingly, the method disclosed in the present invention is capable of producing xylenes more efficiently and at a reduced cost than the previously known processes by increasing the yield of xylenes and reducing the size of the vessels.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein.

DETAILED DESCRIPTION OF THE PREFERRED EMBODIMENTS

It has recently been found that a xylene isomerization and ethylbenzene conversion process which decouples the ethylbenzene conversion of $C_8^+$ reformate from the xylene isomerization stage, and ultimate para-xylene recovery, has significant economic advantages over a "conventional" xylene isomerization process. The present invention utilizes a first reactor to convert ethylbenzene (and in preferred embodiments isomerize xylenes to equilibrium) from a $C_8^+$ aromatics feedstock, a product recovery section to remove various non-$C_8$ aromatics, and a second reactor for isomerizing xylenes. In addition, it has also been found that the use of toluene as co-feed improves the recoverable xylene yield from such a scheme. This new method can also be used to improve product yields in existing "conventional" xylene isomerization complexes.

The method of the present invention is intended to convert high percentages of the ethylbenzene present in mixed ethylbenzene-xylene containing feedstocks, while simultaneously minimizing xylene loss and converting xylenes to approximately the thermal equilibrium concentration (i.e., approximately 50 weight percent (wt %) meta-xylene, and 25 wt % each of para- and ortho-xylene). By maximizing the efficiency of an ethylbenzene/xylene isomerization process, the size of the vessels in the process can be reduced and higher percentages of the desired xylene product can be produced.

Figure 1:
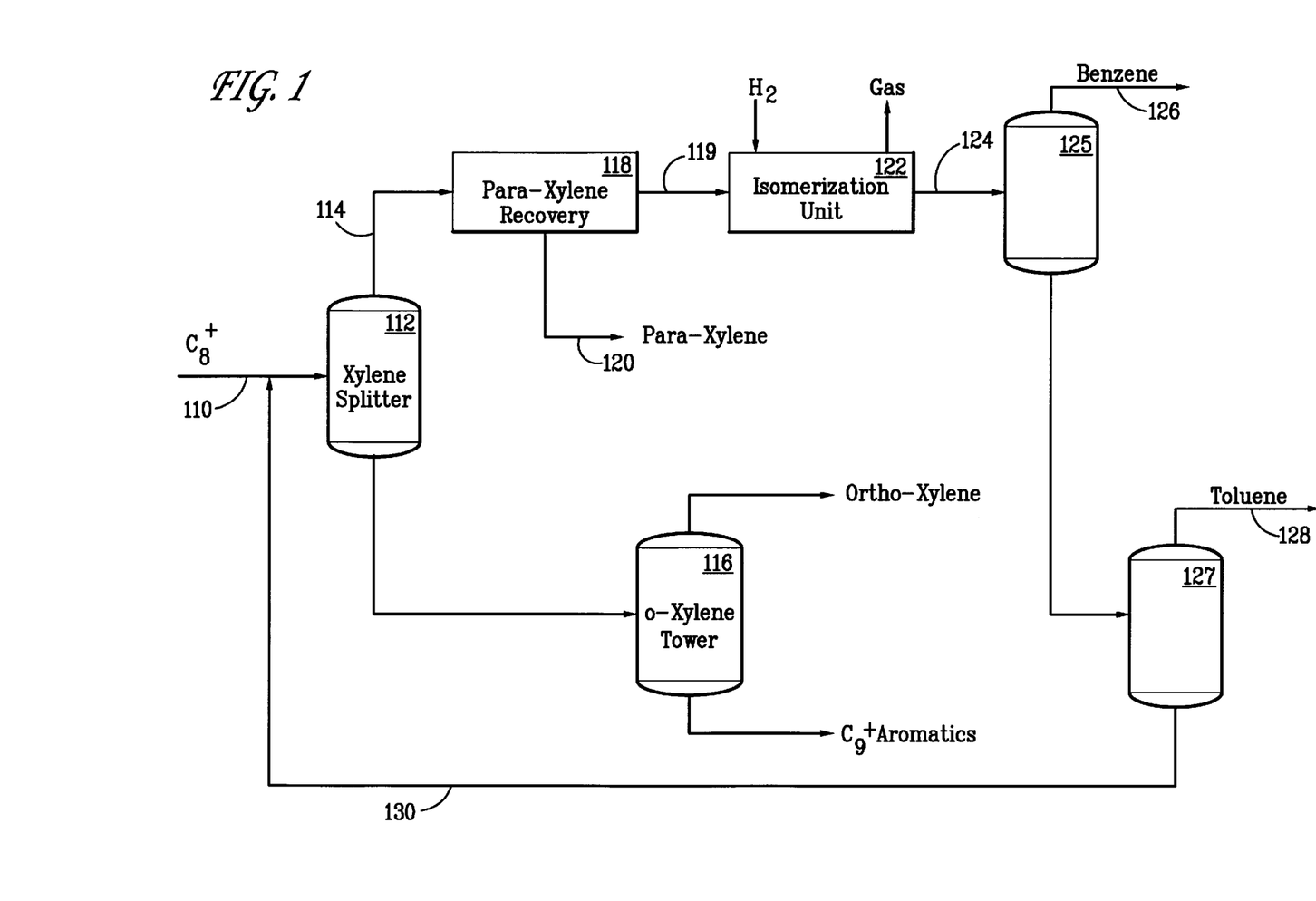
FIG. 1 is a diagram of an ethylbenzene conversion/xylene isomerization process known in the prior art.

FIG. 1 shows a xylene isomerization process known in the prior art wherein a feedstock 110 made up of $C_8^+$ aromatics is fed into a xylene splitter 112, which removes $C_9^+$ aromatics and ortho-xylene from the main feed stream 114. The $C_9^+$ aromatics and ortho-xylene are separated in an ortho-xylene tower 116 and taken off from the process as by-products. The main feed stream 114 is then processed in a para-xylene recovery unit 118 where para-xylene is removed from the feedstock as a product 120. The feedstock is processed in an isomerization unit 122 where xylenes in the feedstock are converted to the thermal equilibrium concentration and ethylbenzene may be converted to lower order aromatics. Benzene 126 and toluene 128 are separated from the effluent of the isomerization unit 124 and the depleted effluent 130 is recycled back into the feedstock 110, upstream of the xylene splitter 112.

Figure 2:
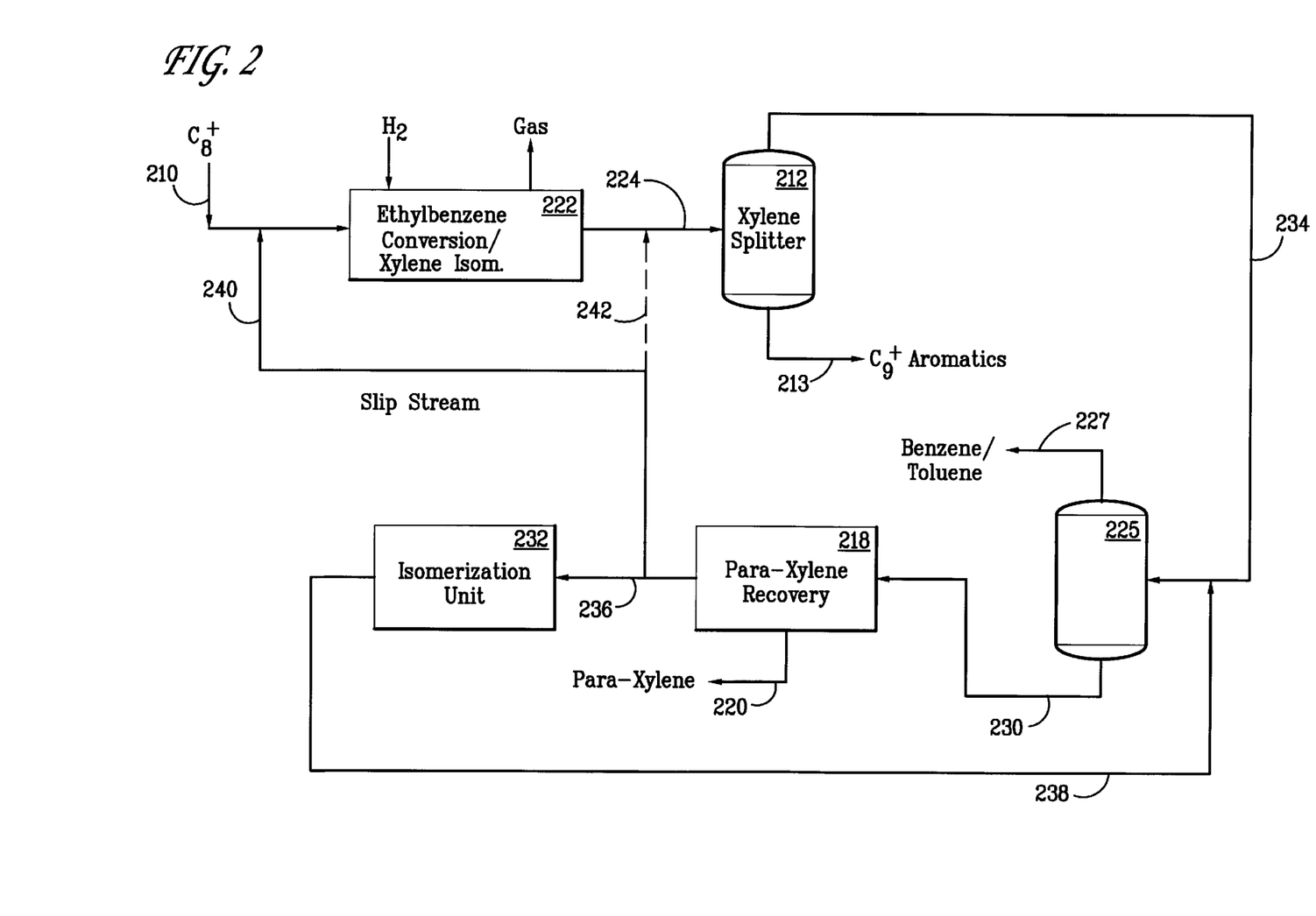
FIG. 2 is a diagram of an ethylbenzene conversion/xylene isomerization process having two stages of xylene isomerization.

FIG. 2 shows a preferred embodiment of the xylene isomerization process of the present invention having a second isomerization stage. A $C_8^+$ aromatics feedstock 210 is fed into an ethylbenzene conversion/xylene isomerization reactor 222 where the ethylbenzene in the feedstock is converted in a first section of the reactor. The feedstock is isomerized in the second section of the reactor and xylenes are converted to the thermal equilibrium concentration. The effluent from the ethylbenzene conversion/xylene isomerization reactor 222 provides a first effluent stream 224 that is sent to a xylene splitter 212, which removes $C_9^+$ aromatics 213 (and in some embodiments of the invention ortho-xylene) as by-products and provides a first depleted stream 234. A separator 225 removes benzene and toluene 227 from the first depleted stream 234 as by-products. The first depleted stream with benzene and toluene removed 230 is processed in a para-xylene recovery unit 218 where para-xylene is removed as a product 220, preferably by selective sorption and/or crystallization. The effluent from the para-xylene recovery unit 218 provides a second depleted stream 236 that is fed to an isomerization unit 232, where xylenes are converted to the thermal equilibrium concentration and most of the ethylbenzene is converted to benzene and ethane. The second effluent stream 238 from the isomerization unit 232 is comprised primarily of xylenes, in the proportion of approximately 50% meta-xylene, 25% ortho-xylene and 25% para-xylene. The second effluent stream 238 is recycled into the first depleted stream 234, upstream of the benzene/toluene separator 225. The recycling of the xylene rich second effluent stream 238 from the isomerization unit maximizes the production of para-xylene. The size of the para-xylene recovery unit 218 and the isomerization unit 232 can be reduced because the volume of the material treated in these units is reduced by removing $C_9^+$ aromatics and $C_7^-$ aromatics upstream in the process.

In a preferred embodiment of the present invention, a slip stream 240 of the effluent 236 of the para-xylene recovery unit 218 is recycled into the feedstock 210 upstream of the ethylbenzene conversion/xylene isomerization reactor 222. The slip stream 240 provides the advantage of allowing the feedstock 210 to be enriched with $C_8$ aromatics and also provides a means for controlling the recycling of $C_8$ aromatics through the para-xylene recovery unit 218 and the isomerization unit 232. In addition, the slip stream 240 provides a means for removing $C_9^+$ aromatics, and optionally ortho-xylene, from the isomerizer/para-xylene recovery unit stage of the process.

In another preferred embodiment of the present invention, two slip streams 240 and 242 of the second depleted stream 236 from the para-xylene recovery unit 218 are recycled. The first slip stream 240 is recycled into the feedstock 210 upstream of the ethylbenzene conversion/xylene isomerization reactor 222. The second slip stream 242 is recycled into the first effluent stream of the ethylbenzene conversion/xylene isomerization reactor 222. The slip streams 240 and 242 provide the advantage of allowing the feedstock 210 to be enriched with $C_8$ aromatics and also provides a means for removing any $C_9^+$ aromatics that may be present in the second depleted stream from the para-xylene recovery unit 218.

Figure 3:
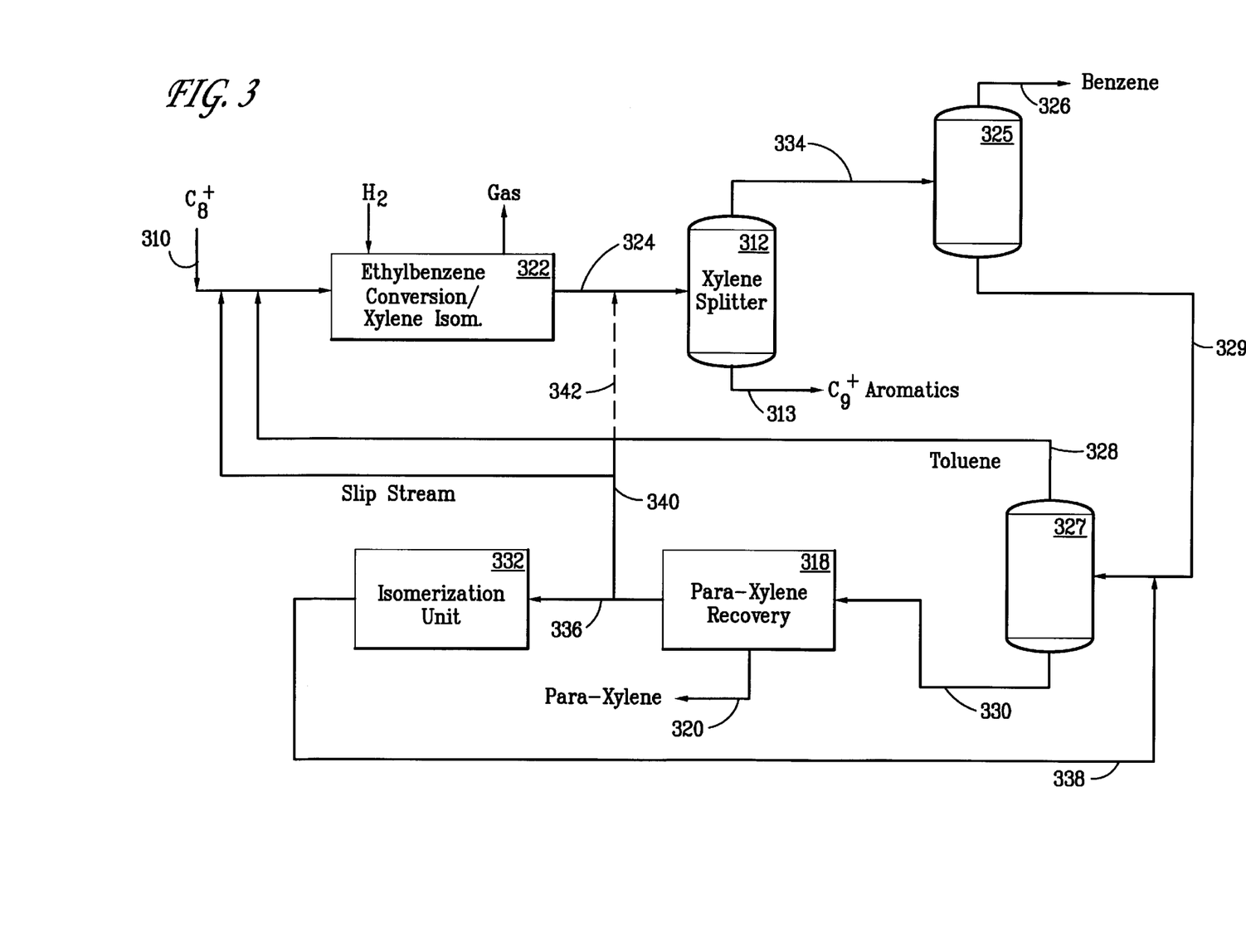
FIG. 3 is a diagram of an ethylbenzene conversion/xylene isomerization process having two stages of xylene isomerization and toluene recycled into the feedstock.

FIG. 3 shows another preferred embodiment of the xylene isomerization process of the present invention which has a second isomerization stage and recycles toluene into the feedstock. A $C_8^+$ aromatics feedstock 310 is fed into an ethylbenzene conversion/xylene isomerization reactor 322 where the ethylbenzene in the feedstock 310 is converted in a first section of the reactor. The feedstock 310 is then isomerized in the second section of the reactor 322 and xylenes are converted to the thermal equilibrium concentration. The effluent from the ethylbenzene conversion/xylene isomerization reactor 322 provides a first effluent stream 324 which is sent to a xylene splitter 312 that removes $C_9^+$ aromatics (and in some embodiments of the invention ortho-xylene) from the first effluent stream 324 as by-products 313 and provides a first depleted stream 334. Separators 325 and 327 are used to remove benzene 326 and toluene 328 from the first depleted stream 334. The first depleted stream with benzene and toluene removed 330 is processed in a para-xylene recovery unit 318 where para-xylene is removed as a product 320. Para-xylene recovery is accomplished by selective sorption and/or crystallization. The effluent from the para-xylene recovery unit 318 provides a second depleted stream 336, which is fed to an isomerization unit 332 where xylenes are converted to the thermal equilibrium concentration and most of the ethylbenzene is converted benzene and ethane. The effluent from the isomerization unit 332 provides a second effluent stream that is recycled into the first depleted stream 329 downstream of the benzene removal stage 326 but prior to the removal of toluene 328. Toluene 328 removed from the first depleted stream 329 downstream of the benzene removal stage 326 is recycled into the feedstock 310 upstream of the ethylbenzene conversion/xylene isomerization reactor 322.

In a preferred embodiment of the present invention, a slip stream 340 of the second depleted stream 336 from the para-xylene recovery unit 318 is recycled into the feedstock 310 upstream of the ethylbenzene conversion/xylene isomerization reactor 322. The slip stream 340 provides the advantage of allowing the feedstock 310 to be enriched with $C_8$ aromatics and also provides a means for controlling the recycling of $C_8$ aromatics through the para-xylene recovery unit 318 and the isomerization unit 332. In addition, the slip stream 340 provides a means for removing $C_9^+$ aromatics, and optionally ortho-xylene, from the isomerizer/ para-xylene recovery unit stage of the process.

In another preferred embodiment of the present invention, two slip streams 340 and 342 of the second depleted stream 336 from the para-xylene recovery unit 318 are recycled. The first slip stream 340 is recycled into the feedstock 310 upstream of the ethylbenzene conversion/xylene isomerization reactor 322. The second slip stream 342 is recycled into the first effluent stream 324 of the ethylbenzene conversion/ xylene isomerization reactor 322. The slip streams 340 and 342 provide the advantage of allowing the feedstock 310 to be enriched with $C_8$ aromatics and also provides a means for removing any $C_9^+$ aromatics that may be present in the effluent of the effluent of the para-xylene recovery unit 318.

In one of the preferred embodiments of the present invention that includes a slip stream 340, the slip stream 340 recycles up to about 50% by weight of the second depleted stream 336 with a most preferred range of about 5% to 25% by weight. The slip stream 340 is recycled into either the feedstock 310 or the first effluent stream 324, depending on the composition of the second depleted stream 336, the composition of the feedstock 310 and the catalysts used in the ethylbenzene conversion/xylene isomerization reactor 322 and the isomerization reactor 332. In a particularly preferred embodiment, two slip streams 340 and 342 from the second depleted stream 336 are recycled into the feedstock 310 and the first effluent stream 324 respectively. In a preferred embodiment, the slip streams 340 and 342 are recycled to the feedstock 310 and to the first effluent stream 324 in a ratio of from about 5 to 1 to about 1 to 1, with a most preferred ratio of about 2 to 1. The amount of flow through the slip streams 340 and 342 to the feedstock 310 and the first effluent stream 324 are selected based on the composition of the second depleted stream 336, the composition of the feedstock 310 and the catalysts used in the ethylbenzene conversion/xylene isomerization reactor 322 and the isomerization reactor 332.

In a preferred embodiment, the toluene concentration of the feedstock 310 is increased by adding toluene to the feedstock 310 to change the composition. In a most preferred embodiment, toluene is added to the feedstock 310 so as to increase the ratio of toluene to xylenes. The toluene can come from an external source or it can be removed from the process downstream of the ethylbenzene conversion unit 322 and recycled into the feedstock 310. After the toluene concentration has been increased, the concentration of toluene in the feedstock 310 is from about 1% to about 25% by weight, with a preferred concentration of about 10% to about 20% by weight.

In another preferred embodiment, in addition to recycling the second depleted stream 336 into the feedstock 310 and/or into the first effluent stream 324 through a slip stream 340 and/or 342, the toluene concentration of the feedstock 310 is increased by adding toluene to the feedstock 310. In this embodiment, the ratio by weight of the slip stream 340 to the toluene that is added is from about 1 to 1 to about 10 to 1, with a preferred ratio of from about 3 to 1 to about 5 to 1.

It has been found that co-fed toluene reduces xylene-losses in ethylbenzene conversion reactions (i.e., in the bed of an ethylbenzene conversion reactor or in the top bed of a dual ethylbenzene conversion/xylene isomerization reactor), from 1.7 wt.% at 90% ethylbenzene conversion without co-fed toluene, to 0.8% with 19% co-fed toluene. In the xylene isomerization unit, co-fed toluene may suppress side reactions such as xylene disproportionation since toluene is one of the products of this reaction. Several process schemes are proposed which take advantage of this finding, including feeding toluene to the ethylbenzene conversion reactor from an outside source, and removing toluene from the effluent stream of the reactor and recycling the toluene into the reactor feedstock. The toluene concentration in the feedstock is increased in order to decrease the conversion of xylenes to lower value products (i.e., trimethyl benzene). When toluene is added to the feedstock and processed in an ethylbenzene conversion reactor, it is believed that toluene may be disproportionated to generate additional xylenes and benzene, and/or to decrease the amount of xylene that is converted.

The toluene concentration in the feedstock can be increased in several different ways so that the feedstock contains at least 5% toluene by weight. The toluene concentration can be increased by adding toluene to the feedstock, either from a source external to the process, or from toluene separated from the process effluent stream of the xylene isomerization stage of the process. When toluene is separated from the effluent stream, it is recycled into the feedstock upstream of the ethylbenzene conversion stage of the process.

The present invention includes both a catalytic process and a separation scheme for producing high-purity para-xylene, which may be incorporated into a new or existing xylene isomerization complex. A conventional xylene isomerization plant, such as that illustrated schematically in FIG. 1, can be modified to provide a process as shown in FIG. 2 by adding an ethylbenzene conversion unit upstream of the xylene splitter 112 and reconfiguring the process streams. The process streams are reconfigured by connecting the light aromatics outlet 114 from the xylene splitter 112 to the inlet of the benzene separation unit 125 downstream of the isomerization unit 122 and connecting the heavy aromatics outlet 130 of the toluene separation unit 127 to the inlet to the para-xylene recovery unit 118. In a preferred embodiment, a slip stream is taken off para-xylene recovery unit effluent 119 and recycled into the feedstock 110 upstream of the ethylbenzene conversion unit. Such a modification would require minimal capital costs, since the "basic" hardware is already in place. Expected savings for a grass roots design would be even greater.

Catalytic Ethylbenzene Conversion and Xylene Isomerization Reactions $C_8$ aromatics feedstock can be contacted with a catalyst under ethylbenzene conversion conditions to produce an ethylbenzene depleted product. The catalyst has been found to produce approximately 12 wt % para-xylene when contacting a feedstock containing 60 wt % meta-xylene, 20 wt % ortho-xylene, and 20 wt % ethylbenzene at a temperature of 426.7° C., a pressure of 150 psig (1136 kPaa), a weight hourly space velocity (WHSV) of 20 hr$^{-1}$, and a hydrogen to hydrocarbon ($H_2$/HC) molar ratio of 1. Optionally, toluene can be co-fed with the feedstock to minimize the depletion of para-xylene from the product. The catalyst may be a silica-bound intermediate pore size molecular sieve that has been modified by being exposed to at least two selectivation sequences, each selectivation sequence includes the steps of contacting the molecular sieve with a selectivating agent and subsequently calcining the selectivated molecular sieve.

One mode of ethylbenzene (EB) reduction is through dealkylation to BZ and ethylene (ETH). This reaction can be represented as:

$$EB \rightarrow BZ + ETH \tag{1}$$

Another reaction for ethylbenzene reduction is through disproportionation to benzene (BZ) and diethylbenzene (DEB). A representation of this reaction is shown in the following equation:

$$EB + EB \rightarrow BZ + DEB \tag{2}$$

The ethylene produced is saturated to ethane using hydrogen in the presence of a hydrogenation catalyst, such as platinum.

Several side reactions may also take place. Representations for some of the side reactions are given below:

$$TOL + TMB \rightarrow XYL + XYL \tag{3}$$

$$TOL + TOL \rightarrow BZ + XYL \tag{4}$$

$$EB + XYL \rightarrow BZ + DMEB \tag{5}$$

$$EB + XYL \rightarrow TOL + MEB \quad (6)$$

$$XYL + XYL \rightarrow TOL + TMB \quad (7)$$

$$ETH + XYL \rightarrow DMEB \quad (8)$$

wherein: XYL is xylene, DMEB is dimethylethylbenzene, TOL is toluene, MEB is methylethylbenzene, and TMB is trimethylbenzene.

Any reaction leading to a decrease of ethylbenzene in the product or ethylbenzene conversion is referred to herein as "ethylbenzene conversion." Moreover, any reaction leading to a decrease of xylenes or xylene conversion is referred to herein as "xylene conversion." Of these reactions, the reactions in equations 1, 2, 3 and 4 are desirable and the reactions in equations 3 and 4 are the most desirable. However, the reaction in equation 3 is limited by the low percentage of trimethylbenzene in typical feedstocks. Further reactions, such as 5, 6, 7, and 8, are not desirable. In addition to the above described reactions, several types of xylene isomerization reactions may occur contemporaneously. Ethylbenzene conversion and xylene loss, as referred to herein, may be determined by comparing the amount of ethylbenzene and total xylenes in the product stream with the amount of those compounds in the feedstock.

Examples of intermediate pore size zeolites useful in this invention include ZSM-5 (U.S. Pat. Nos. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); ZSM-58 (U.S. Pat. No. 4,417,780); and SAPO-5, SAPO-11 and SAPO-41 (U.S. Pat. No. 4,440,871). Also, useful in the practice of the present invention are the catalysts disclosed in U.S. Pat. Nos. 4,899,011 and Re. 31,782. The entire contents of the above references are incorporated by reference herein.

A preferred catalyst for the isomerization stage of the process, such as ZSM-5, comprises an intermediate pore size molecular sieve. Preferred catalyst systems for the ethylbenzene conversion stage of the process are disclosed in U.S. Pat. No. 4,899,011, which is incorporated by reference herein. In a most preferred embodiment, the ethylbenzene conversion catalyst is modified by exposure to at least one selectivation sequence. The selectivation sequence includes the steps of contacting the molecular sieve with a selectivating agent and subsequently calcining the selectivated molecular sieve. The intermediate pore size molecular sieve is combined with a silica binder in an amount sufficient to convert at least 50% of the ethylbenzene present in the $C_8$ aromatic mixture to benzene, xylene, or compounds readily removed by distillation from the $C_8$ aromatic mixture. The conversion of at least 50 wt % of the ethylbenzene present in the feedstock may be considered to produce an ethylbenzene-depleted product.

The catalyst is preferably modified in activity and/or selectivity by at least one modification selected from among ex situ selectivation, in situ selectivation, coke selectivation, steaming, adding a hydrogenation/dehydrogenation functional metal, and combinations thereof, as well as other techniques that are known in the art. For example, the modified catalyst can comprise a silica-bound intermediate pore size molecular sieve, e.g., ZSM-5, which has been ex situ selectivated by being coated with at least one coating of an organosilicon selectivating agent, wherein each coating of selectivating agent is applied to the molecular sieve by a process that includes the steps of contacting the catalyst with the organosilicon selectivating agent present in a liquid carrier and subsequently calcining the catalyst in an oxygen-containing atmosphere. The molecular sieve may be combined with the silica binder before or after being coated with the selectivating agent. The molecular sieve may even be combined with the silica binder between subsequent coatings with the selectivating agent. Optionally, the catalyst can be in situ selectivated by being contacted with an organosilicon selectivating agent in a hydrocarbon feedstock under reactor conditions of temperature, pressure, etc., sufficient to deposit a residue of the organosilicon compound on the catalyst. Coke selectivation can be performed by contacting the catalyst with a decomposable organic compound under conditions sufficient to decompose the organic compound while not damaging the catalyst. Steaming can also be performed to modify the activity of the catalyst as is known in the art. Accordingly, by virtue of selective modification of the catalyst, the isomerization process of the present invention exhibits increased selectivity for ethylbenzene conversion and limited xylene isomerization.

The catalyst of the present invention is especially suitable for the conversion of $C_8$ aromatic streams that contain about 1 wt % to about 60 wt % ethylbenzene, e.g., about 1 wt % to about 50 wt % ethylbenzene. This range spans the range of ethylbenzene concentrations of streams that are derived from a reformer and a pyrolysis gasoline unit. The present process may exhibit cracking of normal and branched paraffins of the type present in unextracted $C_8$ aromatic streams.

The performance of a Pt-containing, steamed, silica selectivated catalyst for this reaction is illustrated below in Example 1. Several choices of catalysts may be made for this reaction. For example, the ethylbenzene conversion reactor would preferably use a diffusionally modified catalyst, such as: variations on the multiply ex situ silica-treated catalysts; in situ selectivated catalysts, such as those achieved by co-feeding silicones along with xylenes feed, or a catalyst generated in situ by co-feeding a selectivating agent in an organic or inorganic carrier; a catalyst which has been modified in the reactor by in situ coking; a catalyst which has been modified by inorganic oxides other than silica, etc. The catalyst systems similar to those taught in U.S. Pat. No. 4,899,011 will also work for this invention, and are a preferred embodiment. These catalysts contain a metal for ethylene saturation, such as Pt, Pd, Re, Rd, Fe, W and Ni. Additionally, catalysts that can convert ethylbenzene to xylenes would be useful here. Included in this would be AlPO's, SAPO's, as well as zeolites. A second catalyst may be employed in this ethylbenzene conversion reactor for isomerizing the entering xylenes to equilibrium. Preferred catalysts for this application include the broad class of molecular sieves, including zeolites, SAPO's, AlPO'S; solid acids such as tungsten zirconia, etc. A preferable catalyst would be ZSM-5 based.

Feedstock

In general, any aromatic $C_8$ mixture containing ethylbenzene and a xylene may be used as feedstock to the process of this invention. Generally, such a feedstock mixture will typically have a $C_9^+$ aromatics content of from about 0 wt % to about 30 wt %, an ethylbenzene content of about 5 wt % to about 50 wt %, an ortho-xylene content of about 0 wt % to about 35 wt %, a meta-xylene content of about 20 wt % to about 90 wt %, and a para-xylene content of about 0 wt % to about 25 wt %. For example, the feedstock may contain about 10 wt % to about 15 wt % ethylbenzene with the balance made up of xylenes and $C_9^+$ aromatics.

Preferably, the feedstock will contain at least about 30 wt %, more preferably at least about 50 wt %, meta-xylene. Feedstocks meeting this standard are termed "meta-xylenerich" feedstocks. For example, the feedstock may comprise about 0 wt % to about 30 wt % $C_9^+$ aromatics, 1 wt % to about 20 wt % ethylbenzene, about 20 wt % to about 80 wt % meta-xylene, about 5 wt % to about 30 wt % ortho-xylene, and about 0.5 wt % to about 20 wt % para-xylene. Alternatively, the feedstock can comprise about 0 wt % to about 30 wt % $C_9^+$ aromatics, 1 wt % to about 20 wt % ethylbenzene, about 50 wt % to about 65 wt % meta-xylene, about 10 wt % to about 30 wt % ortho-xylene, and about 0.5 wt % to about 5 wt % para-xylene.

Toluene can be added as a co-feed to the feedstock contacted with the catalyst to minimize the loss of xylenes, and preferably to increase the xylene content in the effluent. Moreover, the feedstock in addition to the above $C_8$ aromatic mixture may contain non-aromatic hydrocarbons, i.e., naphthenes and paraffins in an amount up to about 30 wt %. In a preferred embodiment, the invention provides means to process a mixture of $C_8$ aromatics such as that derived after other known processing steps.

Process Conditions

In accordance with the present invention, the above described feedstock may be contacted with the catalyst system under suitable conversion conditions to effect ethylbenzene conversion and to minimize xylene losses. Conditions effective to accomplish ethylbenzene conversion are termed "ethylbenzene conversion conditions." Such conversion conditions can include a temperature of about 200° C. to about 550° C., a pressure of from 0 psig to about 1,000 psig, a WHSV of between about 0.1 $hr^{-1}$ and about 200 $hr^{-1}$, and an $H_2$/HC molar ratio of between about 0.2 and about 10. An alternative to these conversion conditions may include a temperature of about 325° C. to about 475° C., a pressure of about 50 psig to about 400 psig, a WHSV of between about 3 $hr^{-1}$ and about 50 $hr^{-1}$, and an $H_2$/HC molar ratio of between about 1 and about 5. The WHSV is based on the weight of catalyst composition, i.e., the total weight of active catalyst and, if used, binder therefor.

To effect high levels of conversion of ethylbenzene, while without excessive loss of xylenes to heavier aromatics and other components, the feedstock should be contacted with the catalyst under the ethylbenzene conversion conditions described above. The conversion process described herein may be carried out as a batch type, semi-continuous, or continuous operation. After use in a moving or fluidized bed reactor, the catalyst can be regenerated, in a regeneration zone in which the coke is burned from the catalyst in an oxygen-containing atmosphere, e.g., air, at an elevated temperature after which the regenerated catalyst is recycled to the conversion zone for further contact with charge stock. In a fixed bed reactor, regeneration can be carried out in a conventional manner by using initially an inert gas containing a small amount of oxygen (0.5 to 2 volume percent) to burn coke in a controlled manner to limit the temperature to a maximum of about 450° C. to 500° C.

One result of the process of this invention is the conversion of 15% to 100% of the ethylbenzene contained in the mixed xylene feedstock to benzene, toluene and other components that are more easily removed from the mixed xylene stream. For example, ethylbenzene conversion levels of greater than 50% are easily accomplished, e.g., greater than 70%, e.g., greater than 80%, e.g., greater than 85%, e.g., 90% or more by weight. The high conversion of ethylbenzene using the selective catalyst and conversion conditions of the present invention results in a molar ratio of benzene produced to ethylbenzene consumed of greater than 0.5, e.g., greater than 0.65, e.g., greater than 0.75, e.g., greater than 0.80.

EXAMPLE 1

To promote ethylbenzene conversion and to isomerize xylenes to equilibrium, a silica-bound catalyst was modified by being exposed to a series of four ex situ selectivation treatments, wherein each treatment comprised contacting the catalyst with 7.8 wt % Dow-550 in decane, followed by drying, and sequential calcination in nitrogen and then air. The four-times treated catalyst was then impregnated with an aqueous solution of platinum ($Pt(NH_3)_4(NO_3)_2$) using an incipient wetness impregnation technique to provide about 0.1 wt % Pt. The catalyst was then dried, calcined in air at 350° C. for 4 hours, and steamed at 990° F. (532° C.) for 3 hours.

Two grams (2 g) of the catalyst were mixed with 6 g of sand and loaded into a ⅜" diameter, stainless steel tube reactor. The reactor was pressurized with nitrogen ($N_2$) to 200 psig, and was then heated to 350° C. Nitrogen feed was then terminated and 100 cc/min hydrogen ($H_2$) was fed to the reactor. This reduction was continued for 1 hour. The temperature inside the reactor was then raised to 800° F. (427° C.) and a $C_8$ hydrocarbon feed was introduced. The feed was blended, and was alumina-percolated prior to use. A feed analysis is summarized in Table 1, below, along with pertinent catalytic data.

TABLE 1

ETHYLBENZENE CONVERSION AND
XYLENE ISOMERIZATION EVALUATION

|  | Sample No. 1 | Sample No. 2 |
|---|---|---|
| Conditions |  |  |
| WHSV ($hr^{-1}$) | 5 | 10 |
| Temperature (° C.) | 760 | 760 |
| $H_2$/HC | 1 | 1 |
| Pressure (psig) | 200 | 200 |

|  | Feed (wt %) | Product (wt %) | Product (wt %) |
|---|---|---|---|
| Composition |  |  |  |
| $C_5^-$ | <0.01 | 2.8 | 2.3 |
| Benzene | <0.01 | 7.1 | 6.2 |
| Toluene | 0.05 | 3.7 | 2.1 |
| Ethylbenzene (EB) | 13.8 | 1.6 | 3.9 |
| Para-xylene | 12.9 | 11.9 | 12.3 |
| Meta-xylene | 47.0 | 46.7 | 46.9 |
| Ortho-xylene | 26.3 | 26.0 | 26.1 |
| $C_9^+$ | <0.01 | 0.1 | 0.2 |
| EB Conversion | — | 89 | 71 |
| Xylene Loss | — | 1.7 | 1.0 |
| Toluene + $C_9^+$ | — | 3.8 | 2.3 |

This example clearly shows that ethylbenzene can be converted in the presence of xylenes (including significant quantities of para-xylene) with minimal xylene loss. By extension, the use of a catalyst capable of isomerizing xylenes to an equilibrium mixture would be expected to raise the para-xylene content of the product. Further it is reasonable to anticipate that co-processing of a $C_9^+$ fraction as the feed would not significantly affect product yields.

EXAMPLE 2

Xylene isomerization evaluation was conducted using an intermediate pore size zeolite (ZSM-5) catalyst in an automated unit with on-line GC sampling. One gram (1.0 g) of the catalyst was loaded into a ⅜" diameter, stainless steel reactor, using sand as an inert packing material. The reactor was pressurized to 550 psig with $N_2$ and heated to 295° C.

under flowing nitrogen. After introduction of the liquid feed to the reactor, all gas flow was stopped. The feed was blended and alumina-percolated. A feed analysis and associated catalytic data are presented below in Table 2.

TABLE 2

XYLENE ISOMERIZATION EVALUATION

Conditions

| | |
|---|---|
| WHSV (hr$^{-1}$) | 8.8 |
| Temperature (° C.) | 295 |
| H$_2$/HC | 0 |
| Pressure (psig) | 550 |

| | Feed (wt %) | Product (wt %) |
|---|---|---|
| Composition | | |
| C$_5^-$ | <0.01 | 0.0 |
| Benzene | 0.0 | 0.0 |
| Toluene | 0.6 | 0.9 |
| Ethylbenzene | 0.3 | 0.3 |
| Para-xylene | 12.4 | 22.9 |
| Meta-xylene | 59.9 | 52.3 |
| Ortho-xylene | 26.1 | 22.6 |
| C$_9^+$ | 0.7 | 1.0 |
| Xylene Loss | — | 0.5 |
| Para-Xylene/Total Xylenes | — | 23.4 |
| Para Approach (PATE) | — | 95.0 |

These test results clearly demonstrate that xylene can be successfully isomerized in the secondary reactor used in the process of the invention. The test results from Examples 2, in combination with the test results from Example 1, confirm the advantages of a dual loop isomerization scheme such as that described herein and illustrated in FIG. 2.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

What is claimed is:

1. A method for increasing efficiency of xylene isomerization of a C$_8$+ aromatic feedstock in a xylene isomerization processing scheme comprising:

subjecting said feedstock to ethylbenzene conversion in a first stage of said scheme to provide a first effluent stream;

removing C$_9$+ aromatics and, optionally, ortho-xylene, from said first effluent stream to provide a first depleted stream;

removing toluene from said first depleted stream;

optionally removing benzene from said first deleted stream to produce a toluene and optionally benzene depleted stream;

recovering para-xylene from said toluene and optionally benzene depleted stream depleted stream to provide a second depleted stream;

isomerizing xylenes in said second depleted stream to provide a second effluent stream;

recycling said second effluent stream into said first depleted stream prior to removal of toluene; and recycling a slip stream from said second depleted stream into said feedstock.

2. A method according to claim 1, which further comprises adding toluene to said feedstock.

3. A method according to claim 1, wherein said toluene removed from said first depleted stream is added to said feedstock.

4. A method according to claim 1, wherein, a single separator is used to remove benzene and toluene from said first depleted stream.

5. A method according to claim 1, wherein up to 50% of said second depleted stream is recycled into said feedstock.

6. A method according to claim 1, which further comprises recycling a slip stream from said second depleted stream into said first effluent.

7. A method according to claim 1, wherein up to 50% of said second depleted stream is recycled into said first effluent stream.

8. A method according to claim 2, which further comprises recycling a slip stream from said second depleted stream into said first effluent stream.

9. A method according to claim 1, wherein said para-xylene recovery is accomplished by selective sorption and/or crystallization.

10. A method according to claim 1, wherein said ethylbenzene conversion and, optionally, said xylene isomerization utilize an intermediate pore size molecular sieve comprising at least one metal selected from the group consisting of Pt, Pd, Ni, Rd, Fe, W and Re.

* * * * *